(12) United States Patent
Meriläinen

(10) Patent No.: US 6,526,297 B1
(45) Date of Patent: Feb. 25, 2003

(54) METHOD AND APPARATUS FOR QUANTIFYING THE HYPNOTIC COMPONENT OF THE DEPTH OF ANESTHESIA BY MONITORING CHANGES IN OPTICAL SCATTERING PROPERTIES OF BRAIN TISSUE

(75) Inventor: Pekka Meriläinen, Helsinki (FI)

(73) Assignee: Instrumentarium Corp., Helsinki (FI)

( * ) Notice: Subject to any disclaimer, the term of this patent is extended or adjusted under 35 U.S.C. 154(b) by 0 days.

(21) Appl. No.: 09/675,871

(22) Filed: Sep. 29, 2000

Related U.S. Application Data
(60) Provisional application No. 60/157,578, filed on Oct. 4, 1999.

(51) Int. Cl.[7] .................................................. A61B 5/00

(52) U.S. Cl. .......................... 600/310; 600/473; 600/472

(58) Field of Search ................................ 600/309–310, 600/322–324, 473–479; 356/39–42

(56) References Cited

U.S. PATENT DOCUMENTS

| | | | |
|---|---|---|---|
| 4,510,938 A | | 4/1985 | Jobsis et al. |
| 4,775,116 A | | 10/1988 | Klein |
| 4,881,549 A | | 11/1989 | Rhyne |
| 5,386,827 A | | 2/1995 | Chance et al. |
| 5,722,407 A | * | 3/1998 | Klingenbeck-Regn et al. ........................ 600/368 |
| 5,729,333 A | * | 3/1998 | Osten et al. ................... 356/39 |
| 5,779,631 A | * | 7/1998 | Chance ........................ 600/328 |
| 5,919,134 A | * | 7/1999 | Diab ............................ 600/323 |
| 6,240,309 B1 | * | 5/2001 | Yamashita et al. ........... 600/407 |

FOREIGN PATENT DOCUMENTS

| EP | 761161 | 3/1997 |
|---|---|---|
| GB | 2311854 | 10/1997 |

OTHER PUBLICATIONS

Alkire M.T., Haier R.J., Shah N.K., Anderson, C.T., "*Positron emission tomography study of regional cerebral metabolism in humans during isoflurane anesthesia*"; Anesthesiology 1997; 86:549–57.

Alkire, M.T., "*Quantitative EEG correlations with brain glucose metabolic rate during anesthesia in volunteers*"; Anesthesiology 1998; 89:323–33.

Gomersall, C.D., Leung, P.L., Gin, T., Joynt, G.M., Young, R.J., Spoon, W.S., Oh T.E., "*A comparison of the Hamamatsu NIRO 500 and the INVOS 3100 near–infrared spectrophometers*"; Anaseth Intensive Care 1998; 26:548–557.

Schwartz, G., Litscher, G., Kleinert R., Jobstmann, R., "*Cerebral oximetry in dead subjects*"; Neurosurg Anesth 196; 8:189–193.

Tomita, M., "*Chemical and neural control of the cerebral circulation*"; Brain '99: XIXth Int'l. Symposium on Cerebral Blood Flow and Metabolism, Copenhagen, Denmark, Jun. 13–17, 1999. (http://www.ne.jp/asahi/brain99/symposium/).

(List continued on next page.)

Primary Examiner—Eric F. Winakur
Assistant Examiner—Matthew Kremer
(74) Attorney, Agent, or Firm—Andrus, Sceales, Starke & Sawall, LLP

(57) ABSTRACT

A method/apparatus for non-invasively measuring a neurological activity state in the brain of a subject to ascertain, for example, the state of the hypnotic component of the subject's anesthesia. The method/apparatus comprises means for, or the step of, passing light through a portion of the brain of the subject, the light having a characteristic that subjects it to scattering during passage by tissues of the brain, the light scattering capabilities of the brain tissues varying responsive to their neurological activity. The light exiting the brain tissue portion is measured to determine the amount of scattering it has undergone as a measurement of the state of the hypnotic component of the subject's anesthesia. Light having a wavelength in a range of 650–1000 nm, preferably around 800 nm may be used.

31 Claims, 3 Drawing Sheets

OTHER PUBLICATIONS

Owen–Reece, H., Elwell, C.E., Harkness, W., Goldstone, J., Delby, D.T., Wyatt, J.S., Smith, M., "*Use of near infrared spectroscopy to estimate blood flow in conscious and anaesthetized adult subjects*"; Br J Anaesth 1996; 76:43–48.

Lovell, A.T., Owen–Reece, H., Elwell, C.E., Smith, M., Goldstone, J.C., "*Continuous measurement of cerebral oxygenation by near infrared spectroscopy during induction of anesthesia*"; Anesth Analg 1999; 88:554–8.

* cited by examiner

METHOD AND APPARATUS FOR QUANTIFYING THE HYPNOTIC COMPONENT OF THE DEPTH OF ANESTHESIA BY MONITORING CHANGES IN OPTICAL SCATTERING PROPERTIES OF BRAIN TISSUE

CROSS REFERENCE TO RELATED APPLICATION

The present application claims the priority of U.S. provisional patent application, Appln. No. 60/157,578, filed Oct. 4, 1999.

BACKGROUND OF THE INVENTION

The reliable monitoring of the depth of anesthesia has remained as one of the main challenges during the past ten years or so while measurement of most of the other key physiological parameters for comprehensive patient monitoring has practically reached a level of maturity. One of the reasons is that the concept of depth of anesthesia, when applying the modern concept of balanced anesthesia, is not a one-dimensional parameter, but has no less than five components. A balanced high quality anesthesia consists of adequate hypnosis, analgesia, muscle relaxation, suppression of the autonomous nervous system and blockade of the neuromuscular junction. Hypnosis means loss of consciousness down to a level able to guarantee amnesia, i.e. that no memories about the operation appear afterwards. Analgesia means that no pain is felt during the surgery. Sufficient muscle relaxation is required to ensure optimal operating conditions for the surgeon manipulating the tissue. The autonomous nervous system, if not suppressed, causes the patient to respond to surgical activity by shock reaction which affects heavily on the hemodynamics and endocrine system. To keep the patient completely motionless, the neuromuscular junction transmitting the orders from the brain to the muscles needs to be blocked, which means complete paralysis of the body. One practical consequence of the paralysis is that the patient also needs to be connected to a mechanical ventilator because the breathing muscles also become inoperative.

To achieve the state of balanced and adequate anesthesia, several different types of drugs are needed. For hypnosis one needs a drug affecting directly on the brain. Such a drug can be either inhalational anesthetics administered as a vapor into the lungs or intravenous agents infused into the blood circulation. Many of the hypnotically acting drugs also have an useful effect on pain, autonomous nervous system response, and muscle relaxation. However, special, dedicated drugs affect best on pain and neuromuscular blockade. What makes this complex picture even more difficult is that the practices of anesthesia vary from country to country and also among individual anesthesiologists. There are also schools of scientists that emphasize the weight of the components of the anesthesia in differing ways.

The importance of reliable monitoring of the depth of anesthesia has both safety and economy related aspects which are partly coupled one to another. Too light anesthesia and especially waking up in the middle of an operation may become an extremely traumatic experience both for the patient and the anesthesiologist. Unnecessarily deep anesthesia means increased costs in use of drugs most of which are rather expensive. Too deep anesthesia usually also affects the quality of the postoperative period and may increase time required for active recovery care.

Even though the importance of taking care and need to monitor all five components of the anesthesia is widely acknowledged, hypnosis has remained as the most difficult task because it is related to the challenging measurement of the level of consciousness which on a wider context also is a philosophical problem. Technically speaking, however, a solution able to quantify the brain activity on a consistent continuous scale extending from full alertness to maximally deep, but reversible, sleep can be considered adequate for the anesthesia purpose, if it is robust enough for the use of different drug cocktails in different individuals. Traditionally the attempts to develop methods and measurements for this purpose have been based on monitoring the electrical activity of the brain based on the weak biosignals picked up with electrodes on the skull surface. This method is called electroencephalography (EEG).

The complex EEG signal having close to random nature at first sight can be analyzed by many signal processing approaches which have developed to high level sophistication since the early days when the first findings about the change of spectral contents of the EEG signal as related to depth of consciousness were published. Generally speaking the EEG signal moves to lower frequencies when the sleep gets deeper and finally reaches a state called "burst suppression" when the signal is silent most of time with short intermediate bursts of electrical activity. The latest achievement in the EEG processing is the "bispectral index", the BIS by Aspect Medical, which in addition to some conventional spectral analysis methods pays attention to the phase coupling between various EEG frequency pairs produced by nonlinear interaction in the electrical activity. What the actual connection of this component, which might reflect the number of independent "oscillators" in the brain, is to the level of consciousness is not well understood. Therefore, the BIS number on a scale from 100 down to zero when moving from alertness to deepest possible sleep, is a semi-empirical combination of various EEG features based on profound statistical analysis of a wide data base collected during thousands of anesthesias. The BIS is based on the processing of not only the spontaneous EEG activity, but also on evoked potentials, the response of the brain to external stimuli, which have been proposed to be used to monitor the level of consciousness. These may be, for example, audible clicks to the ear, or light electrical impulses to the nerves. The former are called acoustic evoked potentials (AEP) and the latter somatosensory evoked potentials (SSEP).

The generic problem of the EEG and evoked potentials in anesthesia application is the artifacts caused by external electrical interference from the other devices, especially the electrocautery machine, which is known as the electrical knife. Additionally the attachment procedure of the EEG electrodes is often considered as consuming too much time in the streamlined fast modern anesthesia process. An additional drawback related both to raw EEG and evoked potentials is the limited speed of response, because both methods require collection of data for a certain period of time, typically at least 5 seconds, and on the top of that some additional time for computing. This can become a problem especially when trying to detect if the patient is waking up from too light an anesthesia which happens very fast because of the physiological cascade mechanisms involving positive feedback loops.

BRIEF SUMMARY OF THE INVENTION

The purpose of this invention is to present a new approach to quantify the relevant brain activity status and its connection to the level of consciousness especially related to the adequacy of the hypnotic component of the depth of anesthesia. It is based the results of many recent findings of basic brain research which has been able to confirm the close physiological links between the electrical activity of the brain and the functional control of the blood and oxygen delivery to the neurally activated part of the brain. This is also coupled with the local metabolic activity reflected as increased glucose metabolic rate. See articles 1, 2 in the list of references. The methods which have illuminated this field the most include positron emission tomography (PET), functional magnetic resonance imaging (fMRI) and near infrared spectroscopy (NIRS).

Technically the NIRS method differs from the two others mentioned above as being much more simple and less expensive. Human tissue including the brain cortex is transparent for near-infrared (NIR) light into depth of several centimeters. The optical wavelengths suitable for this purpose are typically between 700 and 900 nanometers. The NIR spectroscopy has been employed in commercial devices like the Somanetics Invos 300 and Hamamatsu NIRO 500 with a purpose to monitor oxygenation of the cerebral blood. These devices have been designed primarily to be used during carotic artery surgical procedures to give a warning of development of ischemia on the brain tissue. Recent studies (3,4) have indicated that these two devices seem not to measure the same parameter and either of them may not be fully specific and reliable in measuring the brain tissue oxygenation.

On the other hand, the prior art includes pulse oximeters which have developed to a well established technology, being able to measure non-invasively the oxygen saturation of the hemoglobin in the arterial blood with an accuracy comparable to laboratory blood gas analysis. The idea of the pulse oximeter is to use the pulsation of the arterial blood volume, typically at the finger tip, to extract the information from the arterial blood only, and excluding the venous blood and the tissue effects. Thus it is essentially only the AC-component of the optical signal which is utilized. The pulse oximeter also uses two wavelengths chosen to differentiate maximally between the absorption of the light by oxygenated and non-oxygenated hemoglobin. All the additional information included in the DC component of the optical signal and related to the absorption and scattering by the venous blood and tissue is discarded.

However, the brain tissue structure represents a major challenge for pulse oximetry, since the pulsation of the blood in the high density network of intertwined blood capillaries and neuron branches (axons and dentrites) is highly attenuated. It then becomes very difficult to differentiate between oxygenation of arterial and venous blood and the signal is more like a weighted average of both values. In these conditions one can hypothesize that, regarding the received optical signal, the scattering properties of the tissue become more important than the absorption properties.

The scattering of the light from a medium depends on the density and characteristic dimensions of the microscopically tiny structures or particles, "the scatterers." In the brain these consist of the circulating blood cells, the microcapillaries of the cerebral circulation and the neural cells or the neurons. It has been proven (5) that the regulation of the blood flow in the microvascular bed is coupled with the tissue metabolic demands, which varies with the functional activity. It has also been shown that gaseous nitric oxide, a well known vasodilator, acts as a mediator in this process. When a neuron is activated to perform a task some energy is required for the related electrochemical reaction. This is taken from the blood stream, typically as glucose, and some oxygen is needed for the process to convert the glucose to energy. The ingenious control mechanism of the brain to supply enough oxygen to the activated areas works, in a simplified view, so that the microvessel servicing each neuron is dilated to direct more flow to the cell when NO is released at the moment of activation. The neurons themselves have also been shown to change their physical dimensions by swelling during the activation. The dilation of the vessels also means increased blood volume locally. More blood contains more hemoglobin in the space of interest which also affects on the overall scattering and absorption and the output signal.

These couplings related to the brain activation during anesthesia have been studied recently by the PET method and the images reveal that the rate of glucose metabolism during inhalation anesthesia decreases in a consistent manner both during inhalational and propofol anesthesia (1,2). Additionally, to prove the coupling between metabolic and electrical activity, it was shown that the whole-brain glucose metabolism is practically directly proportional to the EEG based bispectral index BIS and the local variations are small (2). Also a simple single channel (NIRO 500) local NIR oxygenation measurement on the forehead of a subject rapidly and consistently seems to react on the loss of consciousness during induction with some intravenous agents (6,7) even if the amplitude and direction of the response varied between the agents.

The present invention exploits the above mentioned documented findings supporting the existence of a direct coupling between the local brain activation level and the size (diameter) of both the blood microvessels and the neurons, as well as the increasing amount of blood in the measurement space. According to well known physical principles, the changes in the dimension and number of light scatterers of the medium change the optical path of photons from a light emitter to a light detector. This means that the output of the light detector in an arrangement where the light beam has interacted with the brain cortex tissue is proportional to the changes of the functional activation at the illuminated brain tissue site. The special application where this measurement would be of high practical value is the monitoring of the changes in the hypnotic component of the depth or adequacy of anesthesia. Also many critically ill patients in intensive care units require sedation and this method would also be useful in measuring changes in the level of sedation for titration of the sedative drugs.

The technical challenge is to tune the instrument to react primarily on the changes of the tissue scattering and not the oxygenation which is of secondary interest in this context. The molecular absorption coefficients, as a function of wavelength, differ considerable for oxyhemoglobin and reduced hemoglobin. This difference is exploited in pulse oximeters by using two wavelengths with great differences in the absorption. However, around 800 nm the absorption is equal for both and this is called "the isobestic point." This means that by using this wavelength the specificity to measure oxygen saturation is lost and the optical output is mainly dominated by changes in scattering and becomes sensitive for brain activation.

The practical measurement set-up would consist of one light detector and one or more transmitters or emitters. The transmitters can either be semiconductor LED's or diode lasers which both are available for the wavelength around 800 nm, i.e. the isobestic point for hemoglobin. The brain tissue is a very strong scatterer and in addition the light has to transmit the skull bone twice so that the received light signal will be very weak. The photomultiplier tube is the most sensitive detector but state-of-the-art solid-state detectors, like special photodiodes, are also adequate for this purpose. The transmitter-detector set is attached preferably on the forehead of the subject to avoid problems caused by hair. The basic requirements for geometry are defined by the requirement that major part of the effective light path has to interact with the brain tissue and the direct path through the skin layer on the skull has to be minimized. A typical distance between transmitter and detector can be from 1 to 5 cm depending on whether direct backscattering or a longer banana shaped optical pathway is preferred.

BRIEF DESCRIPTION OF THE DRAWING

The invention will be further understood by reference to the following detailed description taken in conjunction with the attached drawing in which.

DETAILED DESCRIPTION OF THE DRAWING

Figure 1:
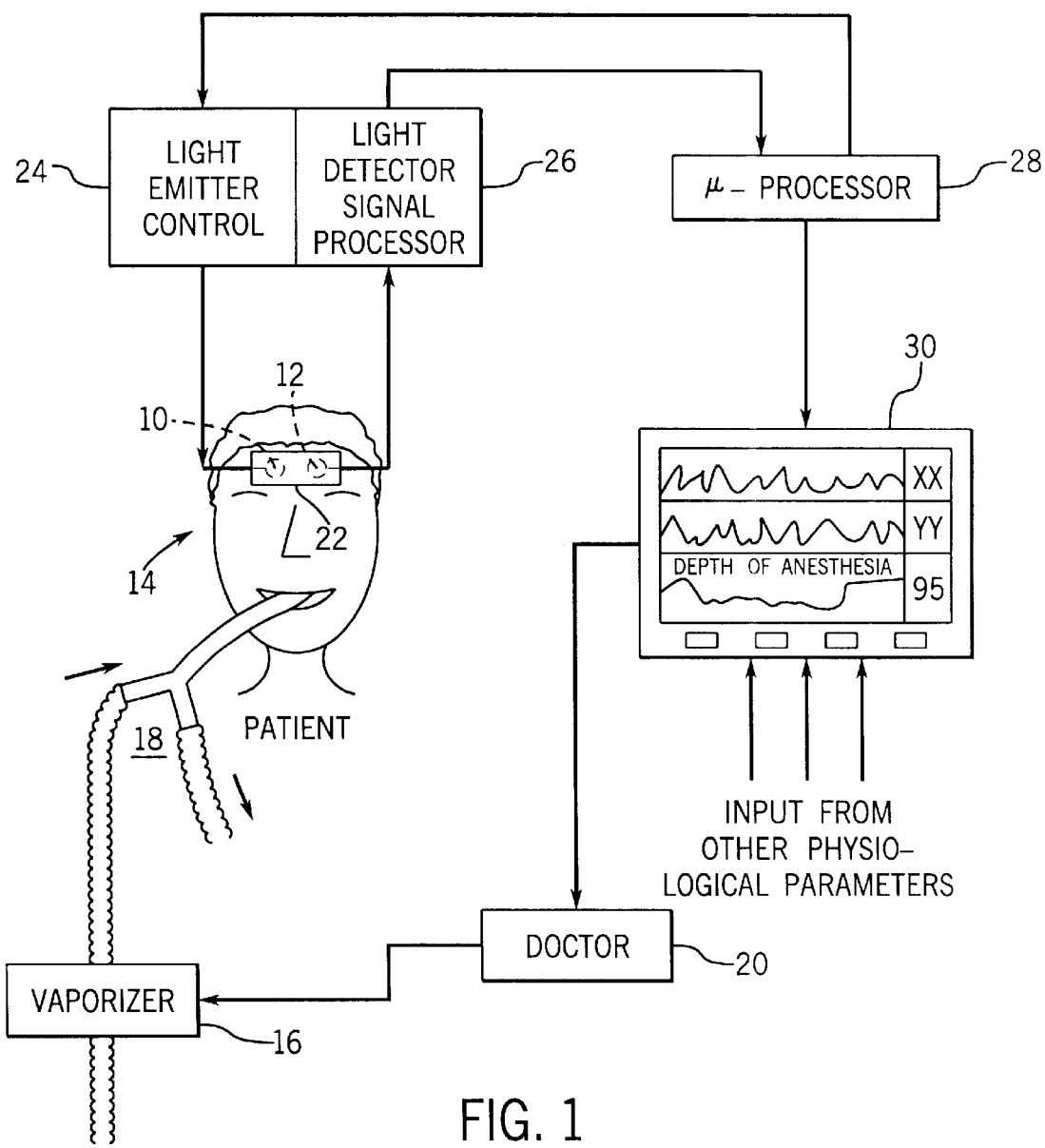
FIG. 1 is a schematic diagram showing the apparatus of the present invention and suitable for carrying out the method of the present invention.

An apparatus of the present invention and suitable for carrying out the method of the present invention is illustrated schematically in FIG. 1. The light transmitter or emitter 10 and light detector 12 are attached on the forehead of an anesthetized, mechanically ventilated patient 14. Light emitter 10 may emit light in a range of 650–1000 nm, preferably around 800 nm. Vaporizer 16 provides anesthetic to the breathing circuit 18 for the patient. The amount of anesthetic supplied by vaporizer 16 is controlled by an attending physician, as indicated by the box 20.

A piece of non-transparent adhesive tape or plaster 22 covers the light emitter and detector and attenuates interference caused by the ambient light. The electronics unit consists of the light emitter controller 24 and the light detector signal processor 26. Controller 24 and processor 26 are connected to microprocessor 28. The light emitter controller 24 can e.g. pulse the emitted light at certain frequency or sequence determined by the microprocessor. The light detector signal processor 26 carries out at least one of amplification and A/D conversion. The light detection can be synchronous with the pulsed light emission. Power for the emitter 10 and detector 12 may be supplied from signal processor 26.

The basic calculations to convert the detected signal to a number characterizing the depth of the hypnotic component of anesthesia are performed by microprocessor 28, which sends the results to display unit 30. The display unit may also show the additional information related to the adequacy of anesthesia or other physiological parameters of interest. Based on the displayed information the doctor 20 responsible for the adequacy of anesthesia can make decisions to adjust the output of vaporizer 16 and/or other drug delivery units (not shown), such as an infusion pump for administration of intravenous agents, to either increase or decrease the depth of anesthesia in patient 14. In addition it should be understood that instead of the open-loop system controlled by the doctor, an automatic controller to run the entire system on a closed-loop basis is also possible.

Figure 3:
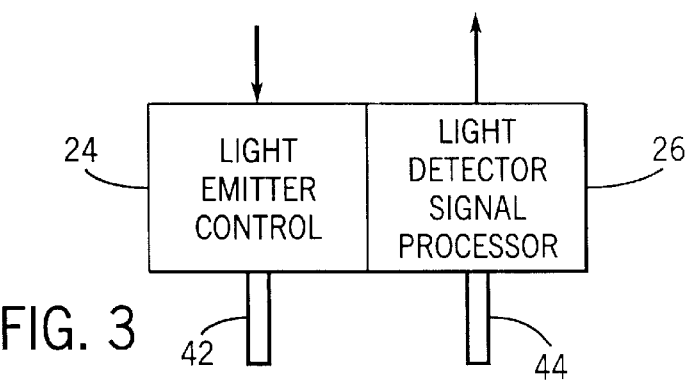
FIG. 3 is a partial, schematic diagram showing a modification of the apparatus of the present invention.
Figure 2:
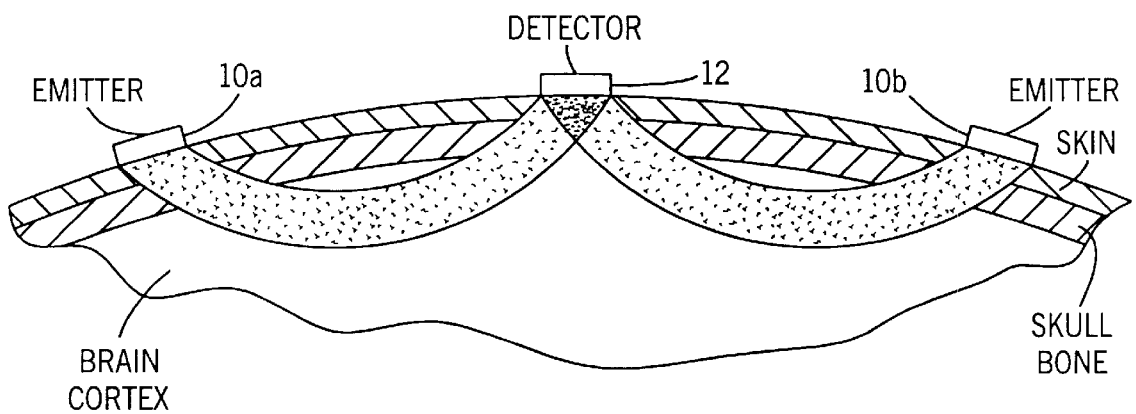
FIG. 2 is a partial cross section view of the skull showing the passage of light through brain tissue.
Figure 4:
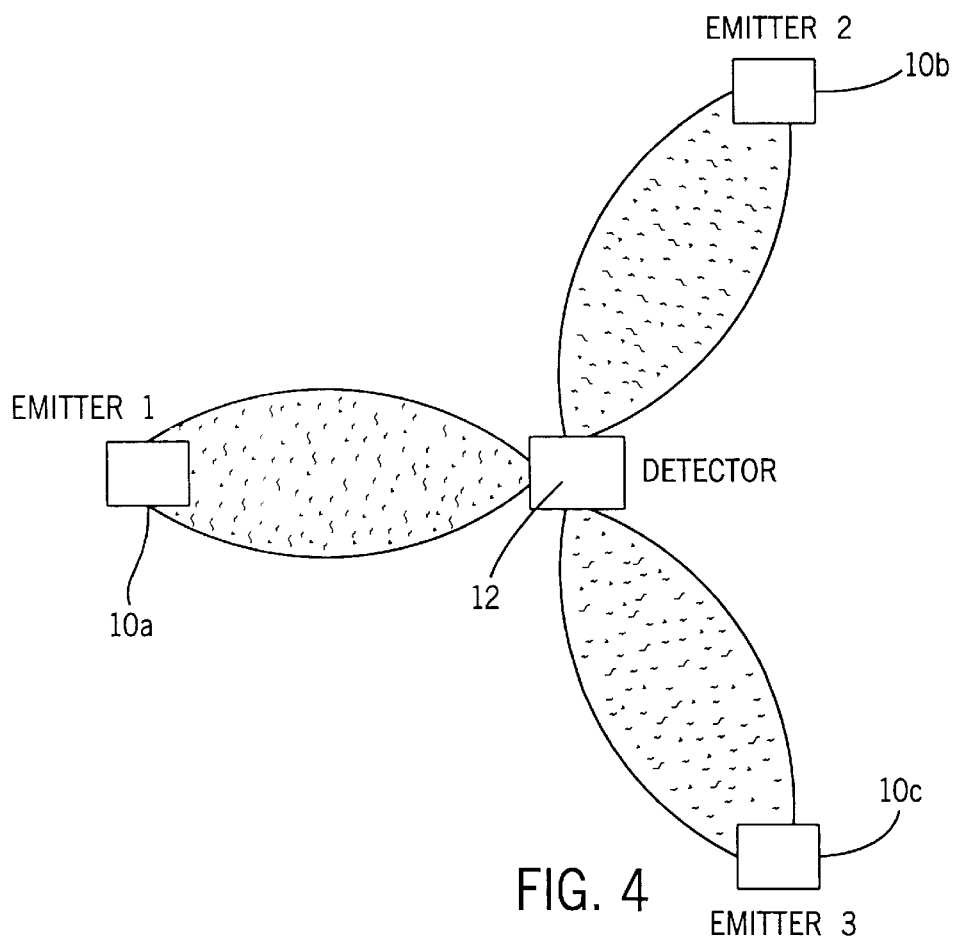
FIG. 4 is a top view taken along the line 3—3 in FIG. 2 showing an arrangement for the emitters and a detector on the skin and showing the light paths through the brain tissue as projected on the skin.

An arrangement using two identical emitters 10a, 10b and one detector 12 is shown in FIG. 2. The light emitter and detector, depending on the types, can be in direct contact of the skin of the patient, as shown in FIG. 1, or the light can be transmitted via optical fibers from and to remote components. See FIG. 3 showing optical fibers 40, 42. It is deemed preferable to use more than one emitter in a symmetrical configuration around the detector to improve the reliability of the measurement by covering a wider area of the tissue and utilizing multiplexing to control the consistency of the measurement against artifacts. FIG. 4 shows a three emitter arrangement 10a, 10b, 10c which covers the illustrated star shaped area in the underlying brain tissue. A reverse configuration of detectors and an emitter may also be used.

Figure 5:
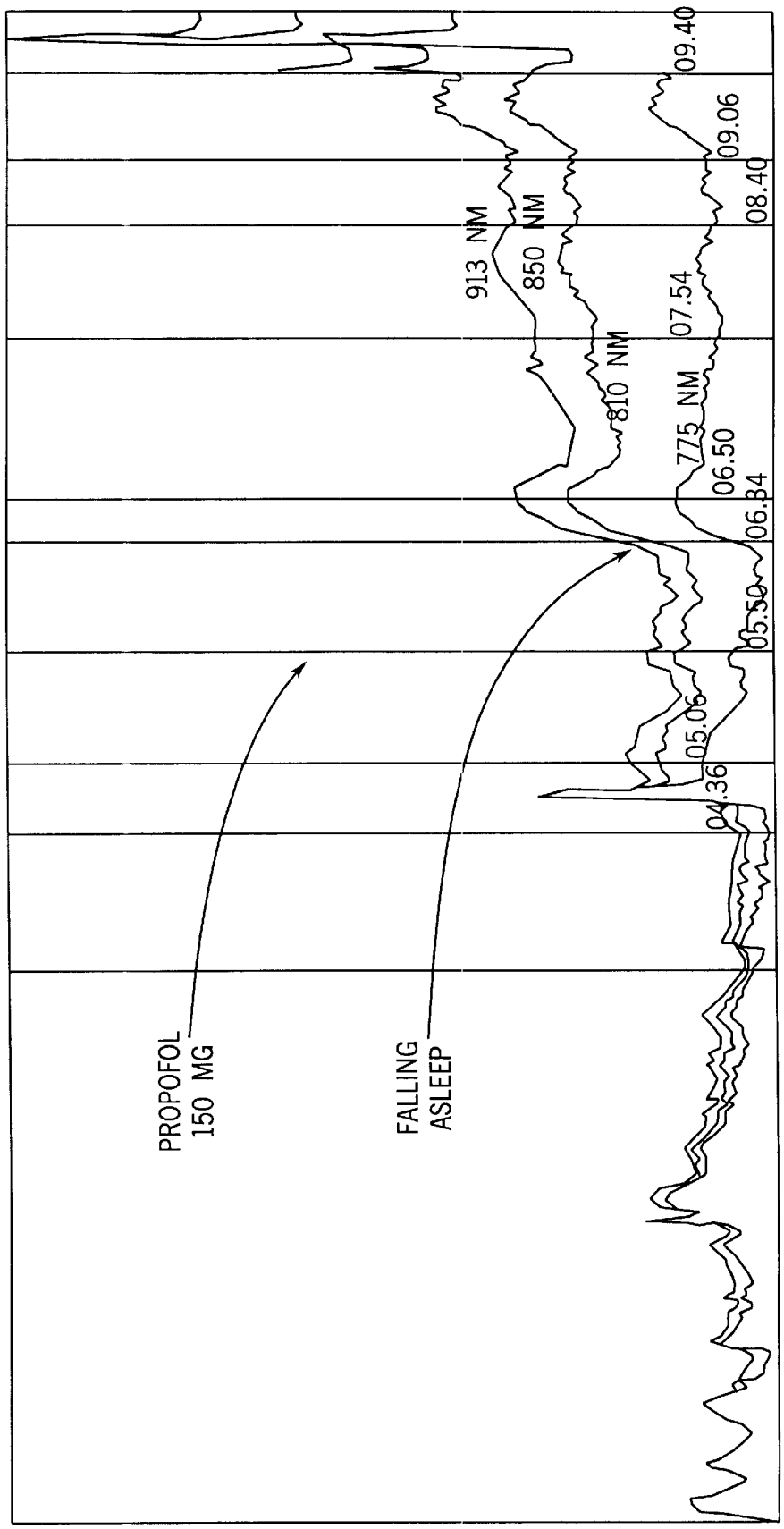
FIG. 5 is a graph showing test results obtained through practice of the present invention.

FIG. 5 shows an example of the practice of the present invention showing the validity of the basic concept. Testing was carried out using a commercially available Hamamatsu NIRO 300 device designed primarily for the measurement of a brain tissue oxygenation index. The index is calculated using an information obtained with four wavelengths of laser light propagated through a banana shaped section of the brain tissue behind the skull of the forehead in the manner generally shown in FIGS. 2 and 3. To this end, light emitters and detectors were applied to the forehead of the subject in the manner generally shown in FIG. 1. The raw signals from the receiving detector for each of the wavelengths (775, 810, 850 and 913 nm) is available from the instrument.

The four output signals were measured during the induction phase of routine anesthesia while an anesthesiologist was recording the moment when the patient lost consciousness with a standard observational method, such as one of those described in the introductory portions of this specification. The results are shown in FIG. 5. A bolus of fast acting "Propofol" intravenous drug was given at a time 5.50 min. from the beginning of the recording. The patient fell asleep according to the anesthesiologist at 6.34 min. The outputs of the detectors started a consistent increase at each of the four wavelengths a little earlier and reached maximal change at 6.50 min. The magnitude of the change was largest at 850 and 913 nm, a little smaller at 810 nm and still smaller at 775 nm. The results suggest that use of the light having essentially wavelengths between 775 and 913 is able to detect a transient change in the optical properties of the brain tissue and hence the transition between consciousness and unconsciousness within a few moments of the transition occurring.

It should be understood that this basic principle can be varied in many ways regarding the geometry and also the value and number of wavelengths, especially if one wants to measure couplings between brain activation, blood volume and oxygenation simultaneously and comprehensively.

Also, while the invention has been described as determining the hypnotic component of anesthesia, it will be readily appreciated that it can also be used on subjects that are unconscious for reasons other than anesthesia and on conscious subjects, as for example to provide a warning that a driver or pilot is falling asleep.

It is therefore recognized that other equivalents, alternatives, and modifications aside from those expressly stated, are possible and within the scope of the appended claims.

LIST OF REFERENCES

1. Alkire M. T., Haier R. J., Shah N. K., Anderson, C. T., *"Positron emission tomography study of regional cerebral*

*metabolism in humans during isoflurane anesthesia*"; Anesthesiology 1997; 86:549–57.
2. Alkire, M. T., "*Quantitative EEG correlations with brain glucose metabolic rate during anesthesia in volunteers*"; Anesthesiology 1998; 89:323–33.
3. Gomersall, C. D., Leung, P. L., Gin, T., Joynt, G. M., Young, R. J., Spoon, W. S., Oh T. E., "*A comparison of the Hamamatsu NIRO 500 and the INVOS 3100 near-infrared spectrophotometers*"; Anaseth Intensive Care 1998; 26:548–557.
4. Schwartz, G., Litscher, G., Kleinert R., Jobstmann, R., "*Cerebral oximetry in dead subjects*"; Neurosurg Anesth 196; 8:189–193.
5. Tomita, M., "*Chemical and neural control of the cerebral circulation*"; Brain '99: XIXth Int'l. Symposium on Cerebral Blood Flow and Metabolism, Copenhagen, Denmark, Jun. 13–17, 1999. (http://www.ne.jp/asahi/brain99/symposium/).
6. Owen-Reece, H., Elwell, C. E., Harkness, W., Goldstone, J., Delby, D. T., Wyatt, J. S., Smith, M. "*Use of near infrared spectroscopy to estimate blood flow in conscious and anaesthetized adult subjects*"; Br J Anaesth 1996; 76:43–48.
7. Lovell, A. T., Owen-Reece, H., Elwell, C. E., Smith, M., Goldstone, J. C., "*Continuous measurement of cerebral oxygenation by near infrared spectroscopy during induction of anesthesia*"; Anesth Analg 1999; 88:554–8.

What is claimed is:

1. Method for non-invasively measuring neurological activity in the brain of a subject to ascertain a state of hypnosis of an anesthetized subject or a state of sedation of the subject, said method comprising the steps of:
   passing light through a portion of the brain of the subject, the light having a characteristic that subjects it to scattering during passage by tissues of the brain, the light scattering capabilities of the brain tissues varying responsive to their neurological activity;
   sensing light that has passed through the portion of the brain and that has thereafter become available for sensing; and
   measuring the sensed light, in the form it became available for sensing, to determine the amount of scattering present in the sensed light and resulting from the passage of the light through the brain tissue as a measurement of the state of hypnosis or sedation of the subject.

2. The method of claim 1 further defined as passing light, the wavelength of which is in the near infrared range, through a portion of the brain.

3. The method of claim 1 further defined as passing light, the wavelength of which is selected so that the light is subjected to scattering but does not react primarily to the state of oxygenation of the brain tissue.

4. The method of claim 1 further defined as passing light having a wavelength in a range of 650–1000 nm through a portion of the brain.

5. The method of claim 4 further defined as passing light having a wavelength of substantially 800 nm through a portion of the brain.

6. The method of claim 1 further defined as including the steps of emitting light from a source comprised of one of a light emitting diode or a diode laser and passing the emitted light through a portion of the brain of the subject.

7. The method of claim 1 further defined as including the steps of sensing the light that has passed through the portion of the brain by a detector comprised of one of a photomultiplier tube or a photodiode and measuring the sensed light using an output signal of the detector.

8. The method of claim 1 further including the step of attaching a light emitter on a skin surface of the subject.

9. The method of claim 1 further defined as including, the step of transmitting light via optical light conducting means to a skin surface of the subject for passing through a portion of the brain.

10. The method of claim 1 further including the step of attaching a light detector on a skin surface of the subject.

11. The method of claim 1 further defined as including the step of transmitting light via optical light conducting means from a skin surface of the subject.

12. The method of claim 1 further including the steps of emitting light by one or more emitters for passage through the brain tissue portion, sensing light that has passed through the portion of the brain by a single detector, and measuring the sensed light using an output signal of the detector.

13. The method of claim 1 including the steps of emitting light for passage through the brain tissue portion by a single emitter, sensing light that has passed through the portion of the brain by one or more detectors, and measuring the sensed light using an output signal of the one or more detectors.

14. The method of claim 1 including the step of arranging a plurality of means for emitting and sensing light in a pattern having a centrally located one of said means and a plurality of said means located around the central one of said means.

15. The method of claim 1 further defined as including the steps of emitting light as a pulse and synchronously sensing the light that has passed through the portion of the brain.

16. The method of claim 1 further defined as one for additionally measuring the oxygenation of the brain and as including the steps of passing additional light through a portion of the brain tissue, the additional light having wavelength characteristics suitable for oxygenation measurement, and measuring the additional light to determine oxygenation.

17. Apparatus for non-invasively measuring neurological activity in the brain of a subject to ascertain a state of hypnosis of an anesthetized subject or a state of sedation of the subject, said apparatus comprising:
   a light emitter emitting light for passage through a portion of the brain of the subject, the light having a characteristic that subjects it to scattering during passage by tissues of the brain, the light scattering capabilities of the brain tissues varying responsive to their neurological activity; and
   a light detector for sensing light that has passed through the portion of the brain and that has thereafter become available for sensing, said light detector measuring the sensed light, in the form it became available for sensing, to determine the amount of scattering present in sensed light and resulting from the passage of the light through the brain tissue as a measurement of the state of hypnosis or sedation of the subject.

18. The apparatus of claim 17 wherein the light emitter is further defined as emitting light as a pulse and said light detector is further defined as synchronously sensing light that has passed through the portion of the brain.

19. The apparatus of claim 17 further defined as one for additionally measuring the oxygenation of the brain and as including an additional light emitter emitting light for passage through a portion of the brain, the light of said additional light emitter having wavelength characteristics suitable for oxygenation measurement, and a light detector for detecting the light from said additional light emitter exiting the brain tissue portion and for measuring same to determine oxygenation.

20. The apparatus of claim 17 wherein said light emitter is further defined as emitting light, the wavelength of which is in the near infrared range.

21. The apparatus of claim 17 further defined as passing light, the wavelength of which is selected so that the light is subjected to scattering but does not react primarily to the state of oxygenation of the brain tissue.

22. The apparatus of claim 19 wherein said light emitter is further defined as emitting light having a wavelength in a range of 650–1000 nm.

23. The apparatus of claim 22 wherein said light emitter is further defined as emitting light having a wavelength of substantially 800 nm.

24. The apparatus of claim 19 wherein said light emitter is further defined as comprising of one of a light emitting diode or a diode laser.

25. The apparatus of claim 19 wherein said light detector is further defined as comprising of one of a photomultiplier tube or a photodiode.

26. The apparatus of claim 19 wherein said light emitter includes means for attaching the light emitter on a skin of the subject.

27. The apparatus of claim 19 wherein at least one of said light emitter and light detector includes means for transmitting light via optical light conducting means to or from a skin surface of the subject.

28. The apparatus of claim 19 wherein said light detector includes means for attaching the light detector on a skin surface of the subject.

29. The apparatus of claim 19 further defined as including a plurality of light emitters and a single light detector.

30. The apparatus of claim 19 further defined as including a single light emitter and a plurality of light detectors.

31. The apparatus of claim 19 further defined as including a plurality of light emitters and light detectors arranged in a pattern having a centrally located one of said elements and a plurality of said elements located around the central one of said elements.

* * * * *